(12) United States Patent
Ohta et al.

(10) Patent No.: US 12,329,311 B2
(45) Date of Patent: Jun. 17, 2025

(54) CONTROL APPARATUS, DATA ACQUISITION METHOD, AND NON-TRANSITORY COMPUTER-READABLE MEDIUM

(71) Applicant: NEC Corporation, Tokyo (JP)

(72) Inventors: Yuko Ohta, Tokyo (JP); Hiromi Shimizu, Tokyo (JP)

(73) Assignee: NEC CORPORATION, Tokyo (JP)

( * ) Notice: Subject to any disclaimer, the term of this patent is extended or adjusted under 35 U.S.C. 154(b) by 939 days.

(21) Appl. No.: 17/431,848

(22) PCT Filed: Feb. 25, 2019

(86) PCT No.: PCT/JP2019/007124
§ 371 (c)(1),
(2) Date: Aug. 18, 2021

(87) PCT Pub. No.: WO2020/174546
PCT Pub. Date: Sep. 3, 2020

(65) Prior Publication Data
US 2022/0133079 A1    May 5, 2022

(51) Int. Cl.
*A47J 31/00* (2006.01)
*A47J 31/44* (2006.01)
*A47J 31/52* (2006.01)
*G01N 33/00* (2006.01)

(52) U.S. Cl.
CPC ............ *A47J 31/525* (2018.08); *A47J 31/44* (2013.01); *G01N 33/0062* (2013.01); *G01N 33/0073* (2013.01); *A47J 31/521* (2018.08)

(58) Field of Classification Search
CPC .......... A47J 31/44; A47J 31/52; A47J 31/521; A47J 31/525; G01N 5/02; G01N 27/12; G01N 29/022
See application file for complete search history.

(56) References Cited

U.S. PATENT DOCUMENTS

| | | | |
|---|---|---|---|
| 11,333,364 B2 * | 5/2022 | Castillo | A23L 5/13 |
| 2018/0088095 A1 * | 3/2018 | Byron | G01N 33/02 |
| 2019/0236678 A1 * | 8/2019 | Wilkinson | G06Q 30/0631 |
| 2020/0405088 A1 * | 12/2020 | Takahashi | A47J 31/446 |
| 2021/0231534 A1 * | 7/2021 | Ohta | G01M 99/00 |

FOREIGN PATENT DOCUMENTS

| | | | | |
|---|---|---|---|---|
| JP | H11-108871 A | | 4/1999 | |
| JP | 2001-104161 A | | 4/2001 | |
| JP | 2012-057981 A | | 3/2012 | |
| JP | 5408580 | * | 2/2014 | G01N 29/022 |

OTHER PUBLICATIONS

International Search Report for PCT Application No. PCT/JP2019/007124, mailed on Apr. 9, 2019.

* cited by examiner

*Primary Examiner* — Reginald Alexander

(57) ABSTRACT

A control apparatus (10) includes a signal detection unit (110) and a data acquisition unit (120). The signal detection unit (110) acquires operation signals relating to an operation of a processing apparatus (20) that processes food and drink, and detects a specific operation signal relating to a specific operation from among the operation signals. The data acquisition unit (120) determines, based on a detection timing of the specific operation signal, a data acquisition period of an odor sensor (30) provided in the processing apparatus (20), and acquires output data being output from the odor sensor (20) during the data acquisition period.

13 Claims, 15 Drawing Sheets

FIG. 8

| KIND | REFERENCE TIME |
|---|---|
| HOT COFFEE | 45[s] |
| ICED COFFEE | 60[s] |
| HOT CAFFE LATTE | 50[s] |
| ICED CAFFE LATTE | 70[s] |
| ... | ... |

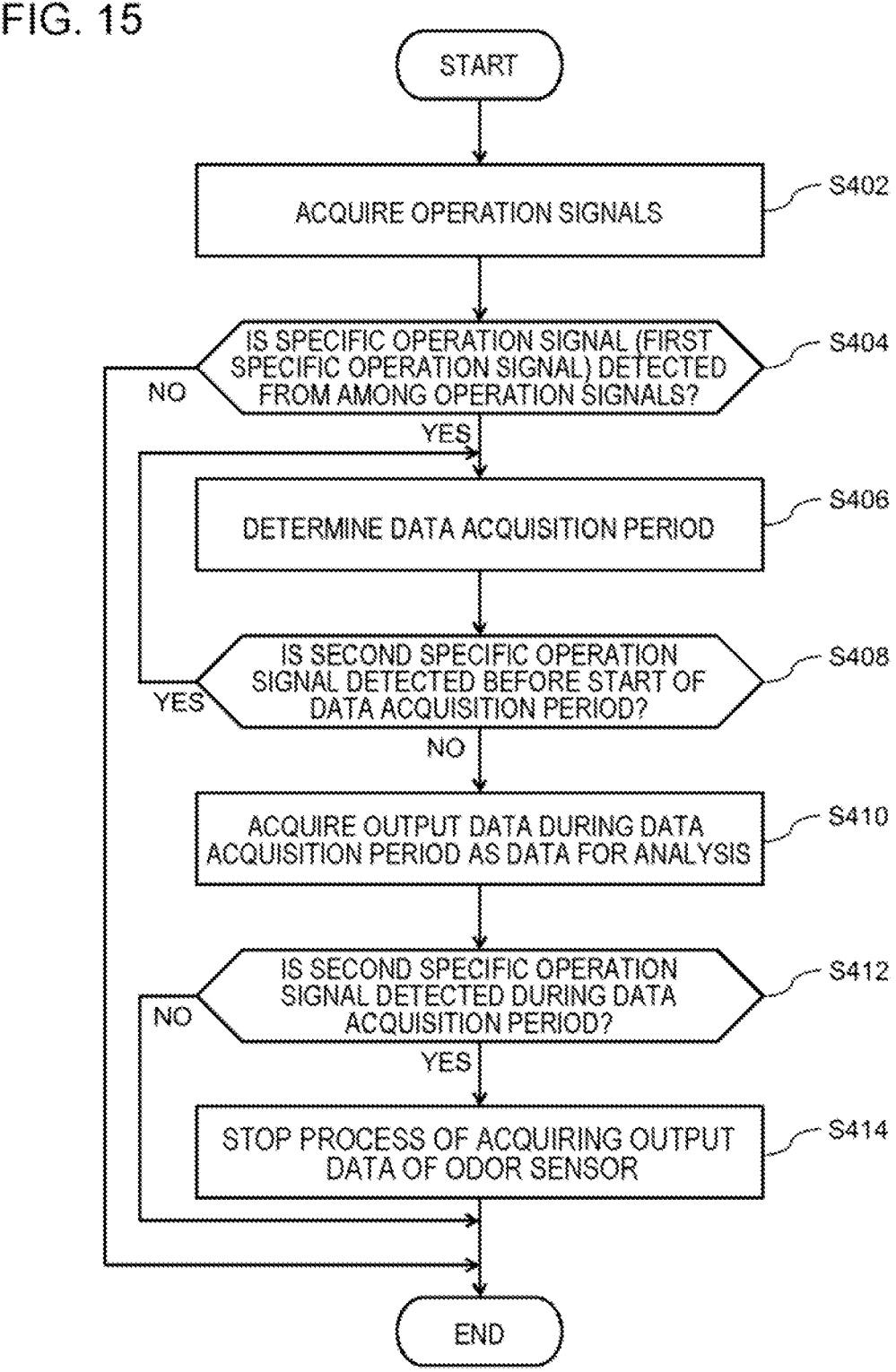

CONTROL APPARATUS, DATA ACQUISITION METHOD, AND NON-TRANSITORY COMPUTER-READABLE MEDIUM

This application is a National Stage Entry of PCT/JP2019/007124 filed on Feb. 25, 2019, the contents of all of which are incorporated herein by reference, in their entirety.

TECHNICAL FIELD

The present invention relates to a control apparatus, a data acquisition method, and a non-transitory computer-readable medium.

BACKGROUND ART

Analysis technologies using odor sensors which sense odors have been studied. Examples of the analysis technologies using odor sensors are disclosed in, for example, PTL 1 and PTL 2 below. PTL 1 discloses a technology of suppressing degradation of an odor sensor by executing control in such a way that the odor sensor is exposed to odorless substitute air in cases other than when measuring intensity of an odor. PTL 2 discloses a technology of detecting degradation of quality of coffee by disposing an odor sensor in a storage container of coffee extracted by a coffee vending machine and measuring a variation with time of the odor.

CITATION LIST

Patent Literature

[PTL 1] Japanese Patent Application Publication No. 2012-057981
[PTL 2] Japanese Patent Application Publication No. H11-108871

SUMMARY OF INVENTION

Technical Problem

When data (odor data) being output from an odor sensor are utilized for various analyses, precision of the analyses depends on precision of the data being output from the odor sensor. Thus, there is a demand for a technology of acquiring, from the odor sensor, output data which enable high-precision analysis.

In view of the above-mentioned problem, the present invention has been made. One of objects of the present invention is to provide a technology of acquiring, from an odor sensor, output data which enable high-precision analysis.

Solution to Problem

A first control apparatus according to the present invention includes: a signal detection unit that acquires operation signals relating to an operation of a processing apparatus that processes food and drink, and detects a specific operation signal relating to a specific operation from among the operation signals; and a data acquisition unit that determines, based on a detection timing of the specific operation signal, a data acquisition period of an odor sensor provided in the processing apparatus, and acquires output data being output from the odor sensor during the data acquisition period.

A second control apparatus according to the present invention includes:
a signal detection unit that acquires operation signals relating to an operation of a processing apparatus that processes food and drink, and detects a specific operation signal relating to a specific operation from among the operation signals;
a data acquisition unit that acquires output data being output from an odor sensor provided in the processing apparatus, in response to detection of the specific operation signal; and
a data extraction unit that determines a data acquisition period, based on a waveform of the output data acquired by the data acquisition unit, and extracts data for analysis from the output data, based on the data acquisition period.

A first data acquisition method according to the present invention includes, by a computer:
acquiring operation signals relating to an operation of a processing apparatus that processes food and drink;
detecting a specific operation signal relating to a specific operation from among the operation signals;
determining, based on a detection timing of the specific operation signal, a data acquisition period of an odor sensor provided in the processing apparatus; and
acquiring output data being output from the odor sensor during the data acquisition period.

A second data acquisition method includes, by a computer:
acquiring operation signals relating to an operation of a processing apparatus that processes food and drink;
detecting a specific operation signal relating to a specific operation from among the operation signals;
acquiring output data being output from an odor sensor provided in the processing apparatus, in response to detection of the specific operation signal;
determining a data acquisition period, based on a waveform of the acquired output data; and
extracting data for analysis from the output data, based on the data acquisition period.

A non-transitory computer-readable medium according to the present invention stores a program that causes a computer to execute the above-described first data acquisition method or second data acquisition method.

Advantageous Effects of Invention

According to the present invention, it is possible to acquire high-precision output data from an odor sensor.

BRIEF DESCRIPTION OF DRAWINGS

The above-described object, other objects, features and advantageous effects will become clearer by preferred example embodiments to be described below, and the following accompanying drawings.

FIG. 8 is a diagram illustrating an example of information which defines reference times for respective kinds of food and drink provided from a processing apparatus.

FIG. 15 is a flowchart illustrating an example of a flow of a process which is executed by the control apparatus of the fourth example embodiment.

DESCRIPTION OF EMBODIMENTS

Figure 1:
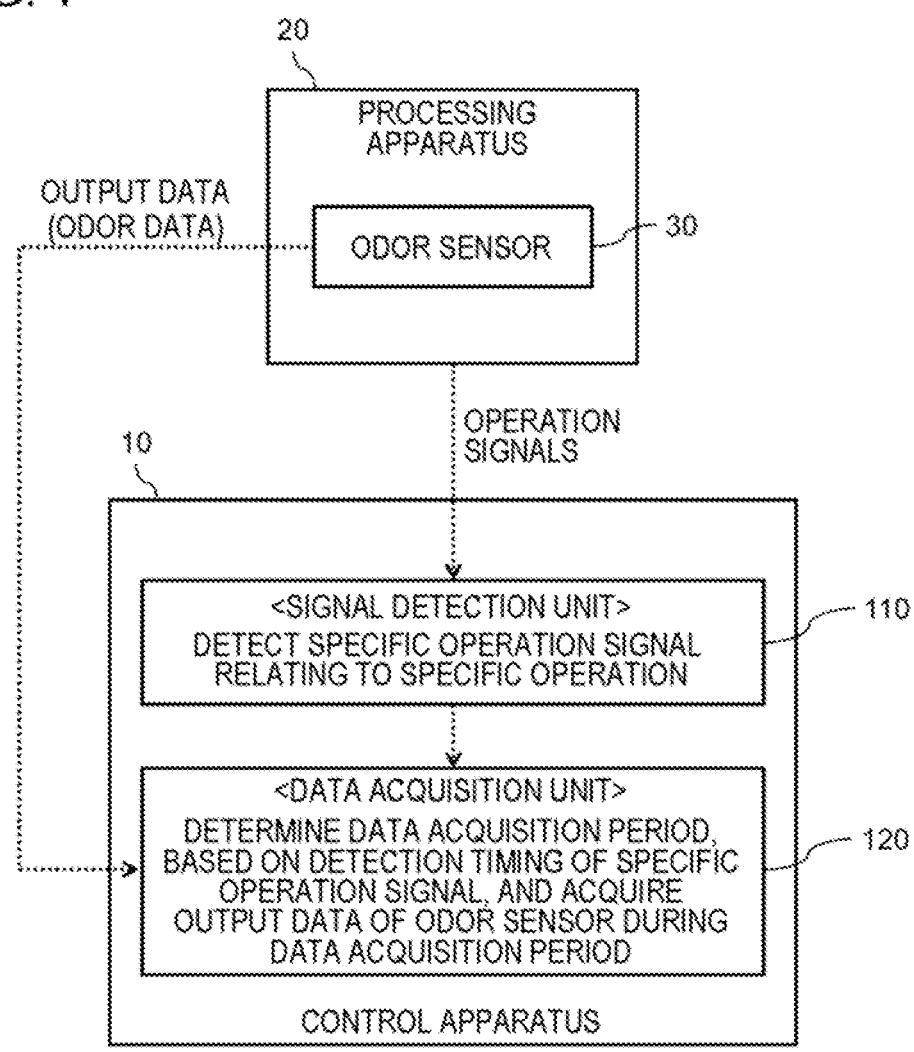
FIG. 1 is a diagram illustrating an outline of an operation of a control apparatus according to a first example embodiment.

Hereinafter, example embodiments of the present invention will be described with reference to the accompanying drawings. Note that in all drawings, similar structural elements are denoted by like reference signs, and a description is omitted unless where necessary. In addition, except where otherwise particularly described, in each block diagram, each block represents not a configuration of a hardware unit, but a configuration of a functional unit. Besides, the direction of an arrow in the drawings is intended to make the flow of information easily understandable, and does not limit the direction of communication (one-way communication/two-way communication) unless otherwise particularly described.

First Example Embodiment

FIG. 1 is a diagram illustrating an outline of an operation of a control apparatus 10 according to a first example embodiment. The control apparatus 10 of the present example embodiment includes a function of acquiring, as data for analysis, output data of an odor sensor 30 provided in a processing apparatus 20.

The processing apparatus 20 is an apparatus which processes food and drink. The processing apparatus 20 includes a function of cooking a drink having an odor, such as coffee or juice, and providing the drink to a purchaser. The odor sensor 30 is provided in the processing apparatus 20 in order to detect the odor occurring by the processing of food and drink by the processing apparatus 20. The odor sensor 30 may be assembled in the processing apparatus 20 as a part of the processing apparatus 20, or may be disposed on the processing apparatus as a unit apparatus separate from the processing apparatus 20.

<Functional Configuration Example of Control Apparatus 10>

As illustrated in FIG. 1, the control apparatus 10 of the present example embodiment includes a signal detection unit 110 and a data acquisition unit 120.

The signal detection unit 110 acquires operation signals of the processing apparatus 20. The operation signals are not particularly limited, if the operation signals are signals relating to the operation of the processing apparatus 20. The operation signals include, for example, a signal which is output in response to an operation of an electronic part (e.g., a button) of the processing apparatus 20; a current signal of the processing apparatus 20, which is acquired by using a current sensor; an acoustic signal relating to an operation sound of the processing apparatus 20, which is acquired by using an acoustic sensor (microphone); and an output signal of the odor sensor 30. In addition, the signal detection unit 110 detects a specific operation signal relating to a specific operation of the processing apparatus 20 from among the operation signals. Here, the "specific operation" is an operation relating to the occurrence of an odor. Concretely, an operation relating to the processing (cooking) of food and drink, which is executed in the processing apparatus 20, is included in the "specific operation".

The data acquisition unit 120 determines, based on a detection timing of the specific operation signal, a period in which an odor occurring by the processing (cooking) of food and drink by the processing apparatus 20 is stabilized, i.e., a period (data acquisition period) for acquiring data from the odor sensor 30. For example, the data acquisition unit 120 sets, as a start point of the data acquisition period, a time point after passage of a reference time from a time point when the specific operation signal is detected. Here, the reference time is a time needed until an output waveform of the odor sensor 30 becomes a stable waveform. Note that the output waveform of the odor sensor 30 is stabilized by the stabilization of the odor occurring in accordance with the operation of the processing apparatus 20 and by the stabilization of the operation of odor molecules (adhesion to a receptor and desorption from the receptor) in the inside of the odor sensor 30. The reference time is determined, for example, based on a result of measurement of an odor component of a target, which is experimentally conducted by using the odor sensor 30. In addition, the data acquisition unit 120 acquires, as data of an analysis target, data (odor data) which are output from the odor sensor 30 during the data acquisition period.

<Advantageous Effect>

In the present example embodiment, the data acquisition period (the period in which the output waveform of the odor sensor 30 is stable) is determined in response to the detection of the specific operation signal of the processing apparatus 20, and the data that are output from the odor sensor 30 are acquired during this period. Specifically, according to the present example embodiment, odor data of a stable waveform, i.e., odor data, with which analysis can be performed with high precision, can be acquired.

<Hardware Configuration Example of Control Apparatus 10>

The control apparatus 10 may be realized by hardware (e.g., a hard-wired electronic circuit) which realizes respective functional structural components, or may be realized by a combination of hardware and software (e.g., a combination of an electronic circuit and a program which controls the electronic circuit). Hereinafter, a further description will be given of the case in which the control apparatus 10 is realized by the combination of hardware and software.

Figure 2:
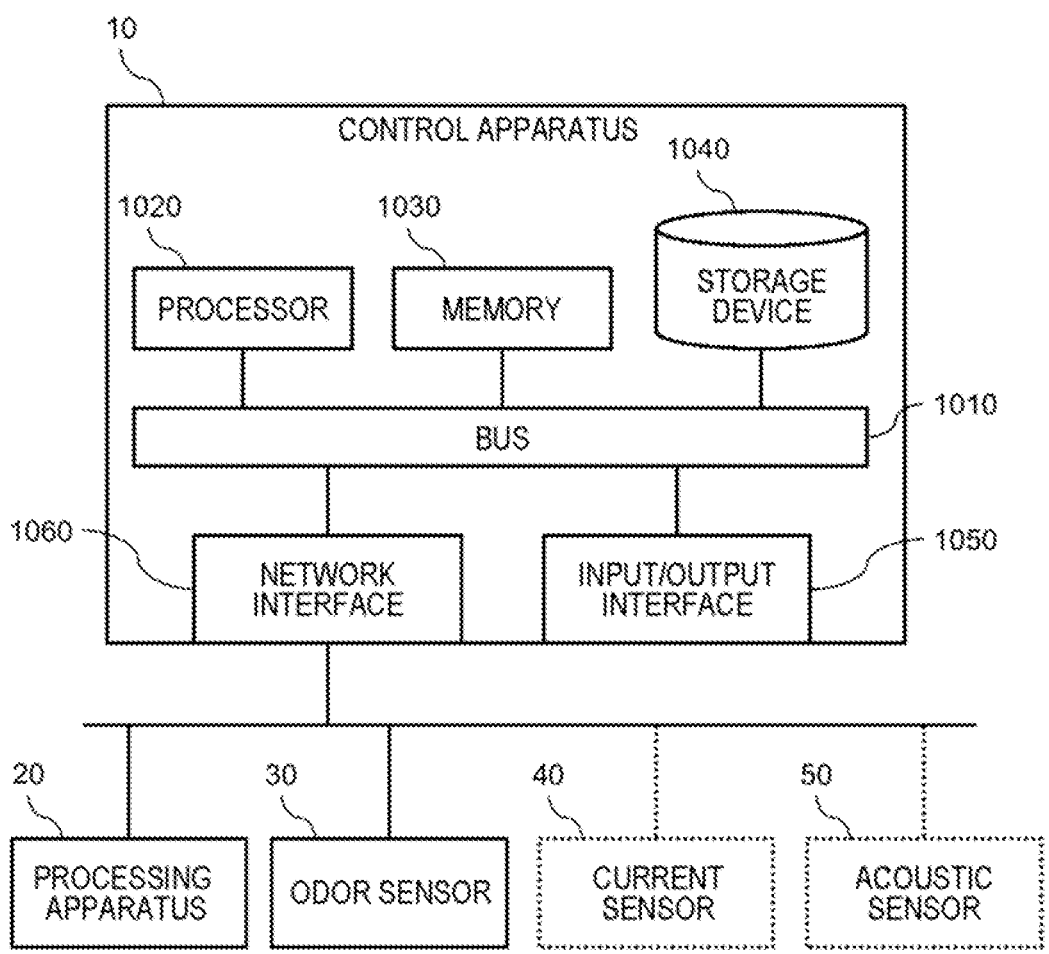
FIG. 2 is a block diagram illustrating a hardware configuration of a control apparatus.

FIG. 2 is a block diagram illustrating a hardware configuration of the control apparatus 10.

The control apparatus 10 includes a bus 1010, a processor 1020, a memory 1030, a storage device 1040, an input/output interface 1050, and a network interface 1060.

The bus 1010 is a data transmission path for mutual data transmission and reception among the processor 1020, memory 1030, storage device 1040, input/output interface 1050, and network interface 1060. It should be noted, however, that the method of mutually connecting the processor 1020, etc. is not limited to the bus connection.

The processor 1020 is a processor which is realized by a CPU (Central Processing Unit), a GPU (Graphics Processing Unit), or the like.

The memory 1030 is a main memory realized by a RAM (Random Access Memory).

The storage device 1040 is a non-transitory computer-readable medium. The storage device 1040 is an auxiliary storage realized by, for example, an HDD (Hard Disk Drive), an SSD (Solid State Drive), a memory card, or a ROM (Read Only Memory). The storage device 1040 stores program modules which realize respective functions (signal detection unit 110, data acquisition unit 120, etc.) of the control apparatus 10. The processor 1020 reads the program modules into the memory 1030, and executes the program modules, thereby realizing the functions associated with the program modules.

The input/output interface 1050 is an interface for connecting the control apparatus 10 and peripheral devices. The peripheral devices include, for example, input devices such as a keyboard and a mouse, and output devices such as a display (touch-panel display) and a speaker.

The network interface 1060 is an interface for connecting the control apparatus 10 to a network. This network is, for example, a LAN (Local Area Network) or a WAN (Wide Area Network). The method in which the network interface 1060 connects to the network may be a wireless connection or a wired connection. The control apparatus 10 is communicably connected to the processing apparatus 20, odor sensor 30, and other external apparatuses via the network interface 1060. For example, as will be described later in detail, when a current sensor 40 or an acoustic sensor 50 is provided in the processing apparatus 20, such devices are communicably connected to the control apparatus 10 via the network interface 1060.

Figure 3:
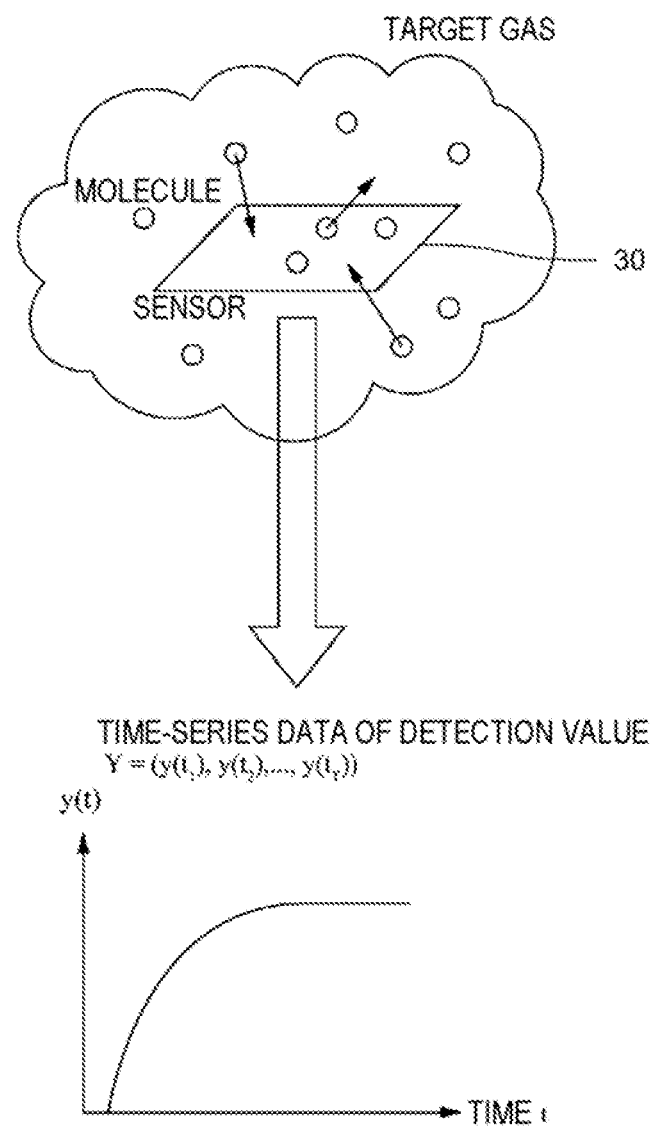
FIG. 3 is a diagram illustrating an example of an odor sensor for acquiring odor data.

Here, as illustrated in FIG. 3, the odor sensor 30 is a senor including a receptor to which molecules (an odor component) included in a gas of a measurement target adhere, and a detection value (output) of the sensor varies in accordance with adhesion and desorption of molecules to and from the receptor. FIG. 3 is a diagram illustrating an example of the odor sensor 30 for acquiring odor data. The odor sensor 30 is, for example, a Membrane-type Surface stress Sensor (MSS). The MSS includes, as the receptor, a functional membrane to which molecules adhere. In addition, a stress occurring in a support member of the functional membrane varies in accordance with the adhesion and desorption of molecules to and from the functional membrane. The MSS outputs a detection value based on the variation of the stress. Note that the odor sensor 30 is not limited to the MSS. It suffices that the odor sensor 30 outputs a detection value, based on a variation of a physical quantity relating to the viscoelasticity or dynamic properties (mass, moment of inertia, and the like) of the member of the odor sensor 30, the variation occurring due to the adhesion and desorption of molecules to and from the receptor. For example, various types of sensors, such as a cantilever type, membrane type, optical type, piezo type, and vibration response type, can be adopted as the odor sensor 30.

<Flow of Process>

Figure 4:
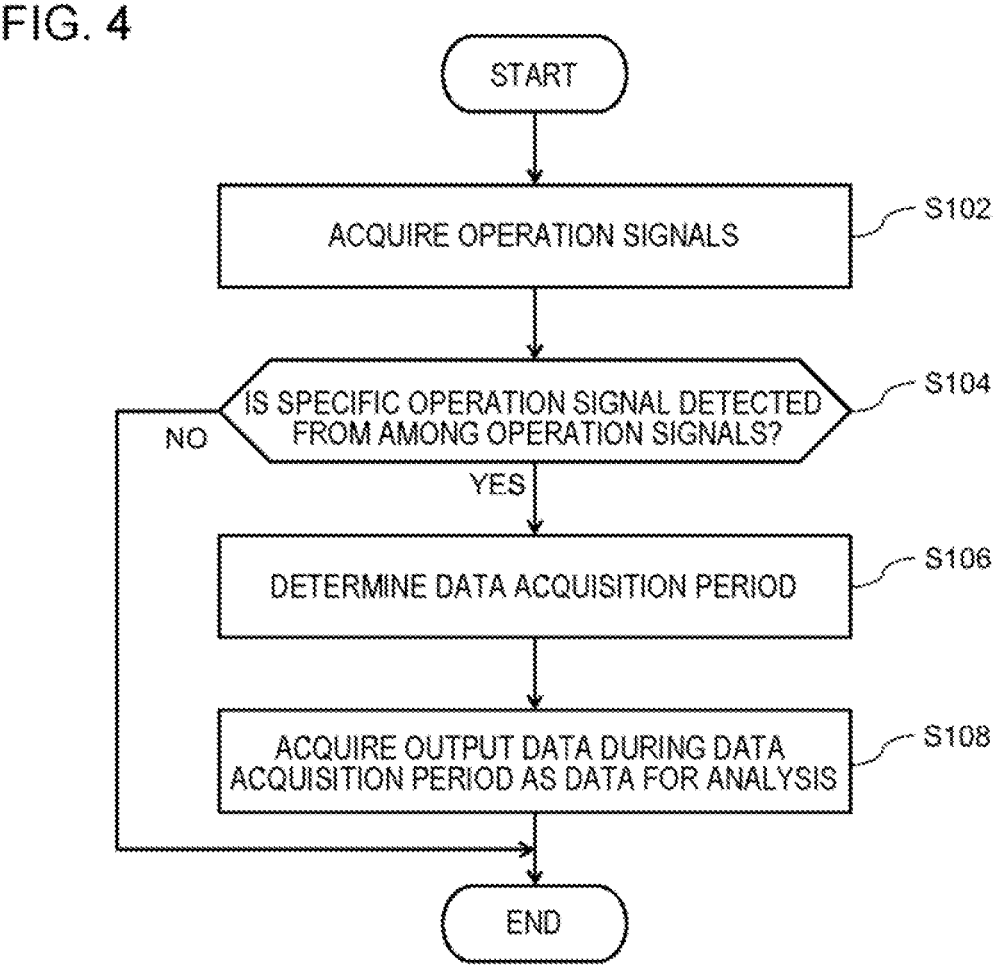
FIG. 4 is a flowchart illustrating a flow of a process which is executed by the control apparatus of the first example embodiment.

FIG. 4 is a flowchart illustrating a flow of a process which is executed by the control apparatus 10 of the first example embodiment.

The signal detection unit 110 acquires operation signals of the processing apparatus 20 (S102). Then, the signal detection unit 110 determines whether or not a specific operation signal is detected from among the operation signals acquired in the process of S102 (S104). Hereinafter, some concrete examples of the flow of detecting the specific operation signal from among the operation signals will be described.

In one example, the signal detection unit 110 detects, as the specific operation signal, a signal (a button depression signal) which is generated in accordance with the depression of a purchase button (not illustrated) of food and drink, which is provided on the processing apparatus 20. For example, when the purchase button of the processing apparatus 20 is depressed, a signal notifying the depression of the purchase button is transmitted from the processing apparatus 20 to the control apparatus 10. The signal detection unit 110 detects, as the specific operation signal, the notification signal which is output from the processing apparatus 20 in response to the depression of the purchase button.

Figure 5:
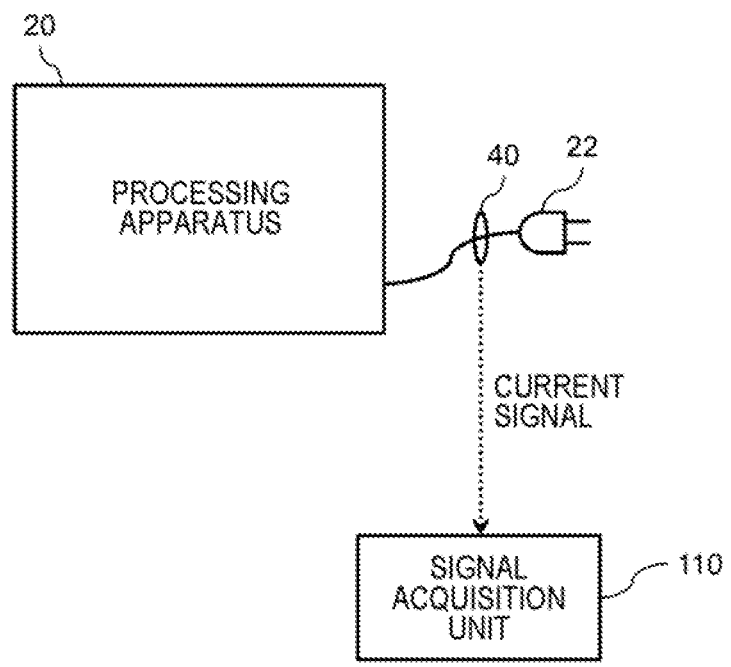
FIG. 5 is a diagram illustrating a concrete example of a flow in which a signal detection unit detects a specific operation signal.

In another example, as illustrated in FIG. 5, when a power line 22 of the processing apparatus 20 is equipped with a current sensor 40, the signal detection unit 110 can acquire, as an operation signal, a current signal of the processing apparatus 20, which is acquired by using the current sensor 40. FIG. 5 is a diagram illustrating a concrete example of the flow in which the signal detection unit 110 detects a specific operation signal. In addition, the signal detection unit 110 can detect the specific operation signal, based on the waveform (so-called "power fingerprint") of the current signal acquired as the operation signal. Specifically, the signal detection unit 110 can determine whether the specific operation signal is included in the acquired current signal, by collating the waveform of the current signal acquired as the operation signal with a sample waveform of the current signal at a time when the processing apparatus 20 is performing a specific operation. In addition, the signal detection unit 110 may be configured to detect the specific operation signal by using a discriminator which discriminates whether an input unknown current signal is the specific operation signal or not and outputs the discrimination result. In this case, the discriminator is constructed by performing machine learning by using learning data in which sample waveforms of various current signals and discrimination labels (e.g., information indicating whether a sample waveform is a specific operation signal or not, or information indicative of the classification of a specific operation signal associated with a sample waveform) are combined.

As a concrete example, a case in which the processing apparatus 20 is a coffee machine will be described. In this case, for example, a database, which stores sample waveforms of current signals at a time when the processing apparatus 20 is performing an operation relating to the occurrence of an odor, is prepared in the storage device 1040 or the like in advance. The current signals at a time when the processing apparatus 20 is performing the operation relating to the occurrence of an odor may include, for example, a current signal at a time an electrically driven mill is being operated, an electric signal at a time when a mechanism for extracting coffee is being operated, and an electric signal at a time when a mechanism for replacing a paper filter after extraction of coffee is being operated. The signal detection unit 110 can determine that the specific operation signal is detected from the current signal, when the waveform of the acquired current signal is collated with sample waveforms stored in the database and, as a result, the waveform indicative of a similarity degree of a threshold or more to any one of the sample waveforms is detected from the current signal.

Figure 6:
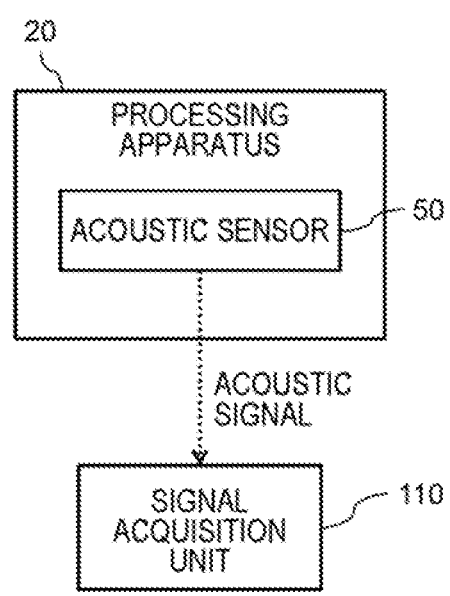
FIG. 6 is a diagram illustrating a concrete example of the flow in which the signal detection unit detects the specific operation signal.

In another example, as illustrated in FIG. 6, when the processing apparatus 20 is equipped with an acoustic sensor (a microphone) 50, the signal detection unit 110 can acquire, as an operation signal, a signal (an acoustic signal) relating to an operation sound of the processing apparatus 20, which is acquired by using the acoustic sensor. FIG. 6 is a diagram illustrating a concrete example of the flow in which the signal detection unit 110 detects a specific operation signal. In addition, the signal detection unit 110 can detect the specific operation signal, based on the waveform of the acoustic signal acquired as the operation signal. Specifically, the signal detection unit 110 can determine whether the specific operation signal is included in the acquired acoustic signal, by collating the waveform of the acoustic signal acquired as the operation signal with a sample waveform of the acoustic signal at a time when the processing apparatus 20 is performing a specific operation. In addition, the signal detection unit 110 may be configured to detect the specific operation signal by using a discriminator which discriminates whether an input unknown acoustic signal is the specific operation signal or not and outputs the discrimination result. In this case, the discriminator is constructed by performing machine learning by using learning data in which sample waveforms of various acoustic signals and discrimination labels (e.g., information indicating whether a sample waveform is a specific operation signal or not, or information indicative of the classification of a specific operation signal associated with a sample waveform) are combined.

As a concrete example, a case in which the processing apparatus 20 is a coffee machine will be described. In this case, for example, a database, which stores sample waveforms of acoustic signals at a time when the processing apparatus 20 is performing an operation relating to the occurrence of an odor, is prepared in the storage device 1040 or the like in advance. The acoustic signals at a time when the processing apparatus 20 is performing the operation relating to the occurrence of an odor may include, for example, an acoustic signal at a time an electrically driven mill is being operated, an acoustic signal at a time when a mechanism for extracting coffee is being operated, and an acoustic signal at a time when a mechanism for replacing a paper filter after extraction of coffee is being operated. The signal detection unit 110 can determine that the specific operation signal is detected from the acoustic signal, when the waveform of the acquired acoustic signal is collated with sample waveforms stored in the database and, as a result, the waveform indicative of a similarity degree of a threshold or more to any one of the sample waveforms is detected from the acoustic signal.

Figure 7:
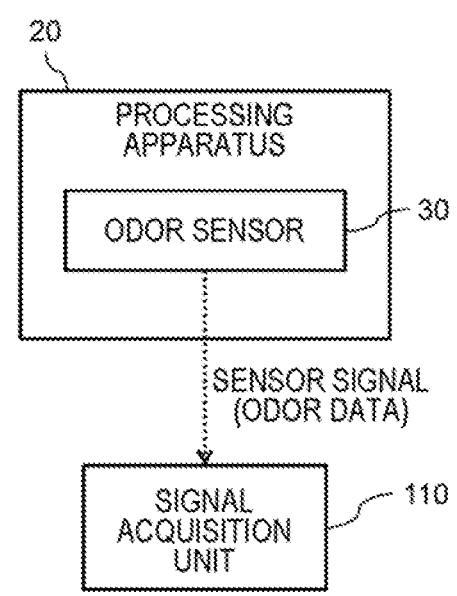
FIG. 7 is a diagram illustrating a concrete example of the flow in which the signal detection unit detects the specific operation signal.

In another example, as illustrated in FIG. 7, the signal detection unit 110 can acquire, as an operation signal, a sensor signal (odor data) of the odor sensor provided in the processing apparatus 20. FIG. 7 is a diagram illustrating a concrete example of the flow in which the signal detection unit 110 detects a specific operation signal. In addition, the signal detection unit 110 can detect the specific operation signal, based on the waveform of the sensor signal (a variation of the detection value of the odor component). Specifically, when the processing apparatus 20 performs an operation relating to the occurrence of an odor, the concentration of the odor component near the processing apparatus 20 increases, and the detection value of the odor sensor 30 increases. Thus, the signal detection unit 110 can determine that the specific operation signal is detected from the sensor signal, when a rising edge of the waveform of the sensor signal of the odor sensor 30 (e.g., a fact that the detection value of the odor sensor 30 has increased to a predetermined threshold or more in a predetermined period) is detected.

Referring back to FIG. 4, when the specific operation signal is detected from among the operation signals (S104: YES), the data acquisition unit 120 determines a period (a data acquisition period) for acquiring odor data which are output from the odor sensor 30 (S106). For example, when the specific operation signal is detected in the signal detection unit 110, the data acquisition unit 120 acquires a detection time of the specific operation signal from the signal detection unit 110. In addition, the data acquisition unit 120 reads out information of a reference time (a time needed until the odor stabilizes after the detection of the specific operation signal). The information of the reference time is prestored, for example, in the storage device 1040 or the like. In addition, the data acquisition unit 120 determines, as a start point of the data acquisition period, a time point after the passage of the reference time from the detection time instant of the specific operation signal. Further, the data acquisition unit 120 determines, as an end point of the data acquisition period, a time point after the passage of a predetermined time from the start point of the data acquisition period.

Then, the data acquisition unit 120 acquires, as data for analysis, output data which are output from the odor sensor 30 during the data acquisition period determined in the process of S106 (S108). The data acquisition unit 120 stores the data acquired in S108 as the data for analysis in a predetermined storage unit such as the storage device 1040.

The output data of the odor sensor 30 acquired by the above process can be utilized for analysis, such as determination of degradation of food and drink provided from the processing apparatus 20, or determination of a maintenance timing of the processing apparatus 20.

<Modification>

Here, the data acquisition unit 120 may be configured to stop the odor sensor 30 until the specific operation signal is detected, and to operate the odor sensor 30 in response to the detection of the specific operation signal. In this manner, by operating the odor sensor 30 only when necessary, an advantageous effect of suppressing degradation of the performance of the odor sensor 30 can be expected. In addition, in this case, the output data of the odor sensor 30 are acquired after the passage of the reference time (the time needed until the output waveform of the odor sensor 30 stabilizes) from the detection time point (≈the start time point of the odor sensor 30) of the specific operation signal. Thus, even when the odor sensor 30 is operated in response to the detection of the specific operation signal, the advantageous effect that high-precision odor data can be acquired is not lost.

In addition, in the processing apparatus 20, there is a case in which a plurality of kinds of food and drink are provided. For example, in a coffee machine or the like, there is case in which a plurality of kinds of coffees, such as iced black coffee, hot black coffee, iced caffè latte, and hot caffè latte, are provided. In this case, there is also a case in which the time until the output waveform of the odor sensor 30 stabilizes varies depending on the kind of food and drink that is provided (concretely, the time needed for processing of food and drink, the temperature of food and drink at the time of providing, or the components included in food and drink). Thus, the reference time, which is used in order for the data acquisition unit 120 to determine the data acquisition period, may be determined in accordance with the kind of food and drink provided from the processing apparatus 20.

In this case, for example, using information as illustrated in FIG. 8, the data acquisition unit 120 can determine the start point of the data acquisition period according to the kind of food and drink. FIG. 8 is a diagram illustrating an example of information which defines reference times for respective kinds of food and drink provided from the processing apparatus 20. The information as illustrated in FIG. 8 is acquired, for example, by experimentally measuring, with use of the odor sensor 30, times needed until odors stabilize in connection with respective kinds of food and drink provided from the processing apparatus 20. Here, when an opening-and-closing door is provided on a take-out port of food and drink provided from the processing apparatus 20, the time needed until the odor stabilizes may include a time in which a user of the processing apparatus 20 opens the opening-and-closing door at the time of taking out food and drink (a theoretically or empirically acquired value).

Specifically, to begin with, when a specific operation signal is detected by the signal detection unit 110, the data acquisition unit 120 determines the food and drink that is provided, in accordance with the specific operation signal. In one example, when the button depression signal is detected as the specific operation signal, the data acquisition unit 120 determines which button is depressed, from the button depression signal, thus being able to determine the kind of food and drink provided from the processing apparatus 20. In addition, when a specific operation signal is detected from the current signal acquired as the operation signal, the data acquisition unit 120 can determine the kind of food and drink provided from the processing apparatus 20, based on the waveform of the specific operation signal. For example, when the processing apparatus 20 is a coffee machine, the mechanism that operates is different between when black coffee is provided and when caffè latte is provided. In addition, the difference of the mechanism that operates appears as a difference of the waveform (power fingerprint) of the current signal. Thus, based on the waveform of the current signal, the data acquisition unit 120 can determine the kind of food and drink provided from the processing apparatus 20. Similarly, when a specific operation signal is detected from the acoustic signal acquired as the operation signal, a difference occurs in operation sound according to the kind of food and drink. Thus, the data acquisition unit 120 can determine the kind of food and drink provided from the processing apparatus 20, based on the waveform of the acoustic signal. In addition, for example, referring to the information as exemplarily illustrated in FIG. 8, the data acquisition unit 120 acquires the reference time associated with the determined kind of food and drink. In one example, when the kind of food and drink provided from the processing apparatus 20 is determined to be "hot coffee", the data acquisition unit 120 can determine, as the start point of the data acquisition period, a time instant which is 45 seconds after the detection time instant of the specific operation signal, by using the reference time of "45 seconds" stored in association with the "hot coffee".

By this configuration, an optimal period, in which the odor stabilizes with respect to each kind of food and drink, can be determined, and the odor data that are output from the odor sensor 30 during this period can be acquired as the data for analysis.

Second Embodiment

A control apparatus 10 of the present example embodiment has a configuration which is different from the configuration of the first example embodiment with respect to the points to be described below.

<Functional Structural Example of Control Apparatus 10>

Figure 9:
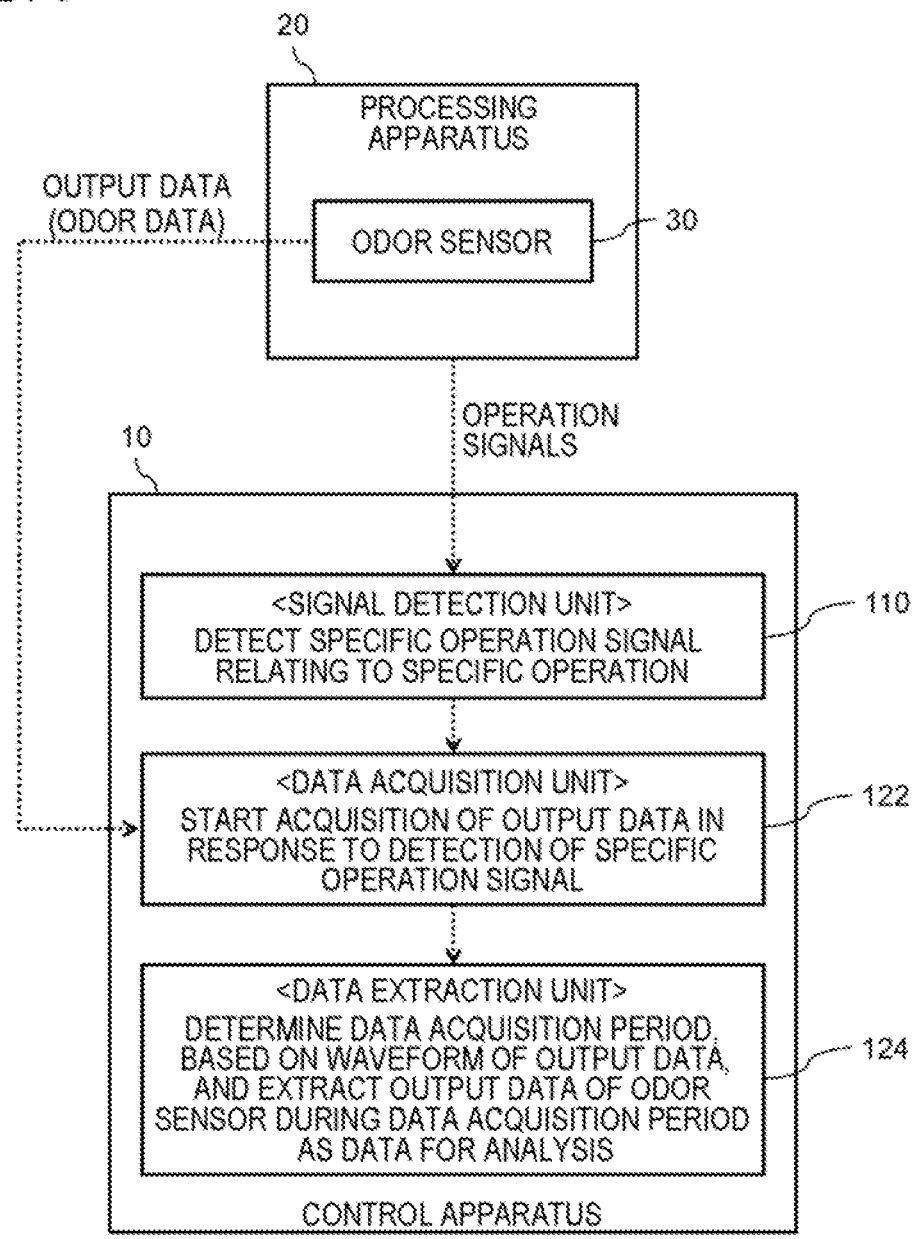
FIG. 9 is a diagram illustrating an outline of an operation of a control apparatus according to a second example embodiment.

FIG. 9 is a diagram illustrating an outline of an operation of a control apparatus 10 according to a second example embodiment. Like the first example embodiment, the control apparatus 10 of the present example embodiment includes a signal detection unit 110. On the other hand, unlike the first example embodiment, the control apparatus 10 of the present example embodiment includes a data acquisition unit 122 and a data extraction unit 124.

The data acquisition unit 122 starts acquisition of output data (odor data) of the odor sensor 30 in response to the detection of a specific operation signal. The data extraction unit 124 determines a data acquisition period, based on the waveform of the output data acquired by the data acquisition unit 122. In addition, the data extraction unit 124 extracts data for analysis from the output data acquired from the odor sensor 30, based on the data acquisition period. Specifically, the data extraction unit 124 sets, as a start point of the data acquisition period, a time point when the waveform meets a predetermined reference with respect to the output data acquired by the data acquisition unit 122. Further, the data extraction unit 124 sets, as an end point of the data acquisition period, a time point after a predetermined time from the start point.

Here, the predetermined reference is a reference for discriminating whether the waveform of output data of the odor sensor 30 is stable or not. Whether the waveform of output data of the odor sensor 30 is stable or not can be determined, for example, based on a variation of the amplitude of the waveform. Specifically, when the variation of the amplitude of the waveform is less than a predetermined reference value, it can be said that the waveform is stable. In this case, the data extraction unit 124 determines whether the output data are stable or not, based on the variation of the amplitude of the waveform of the output data of the odor sensor 30 acquired by the data acquisition unit 122. In addition, when the data extraction unit 124 successfully determines that the output data of the odor sensor 30 are stable, the data extraction unit 124 extracts, as the data for analysis, the output data which are output from the odor sensor 30 after the time point at which this determination is acquired, and stores the extracted data in the storage area such as the storage device 1040.

<Hardware Configuration Example of Control Apparatus 10>

The control apparatus 10 of the present example embodiment has a similar hardware configuration (example: FIG. 2) to the hardware configuration of the first example embodiment. In the present example embodiment, the storage device 1040 stores program modules which realize the functions of the above-described data acquisition unit 122 and data extraction unit 124, in place of the program modules which realize the functions of the data acquisition unit 120. The processor 1020 reads these program modules into the memory 1030 and executes the program modules, thereby realizing the functions associated with the program modules.

<Flow of Process>

Figure 10:
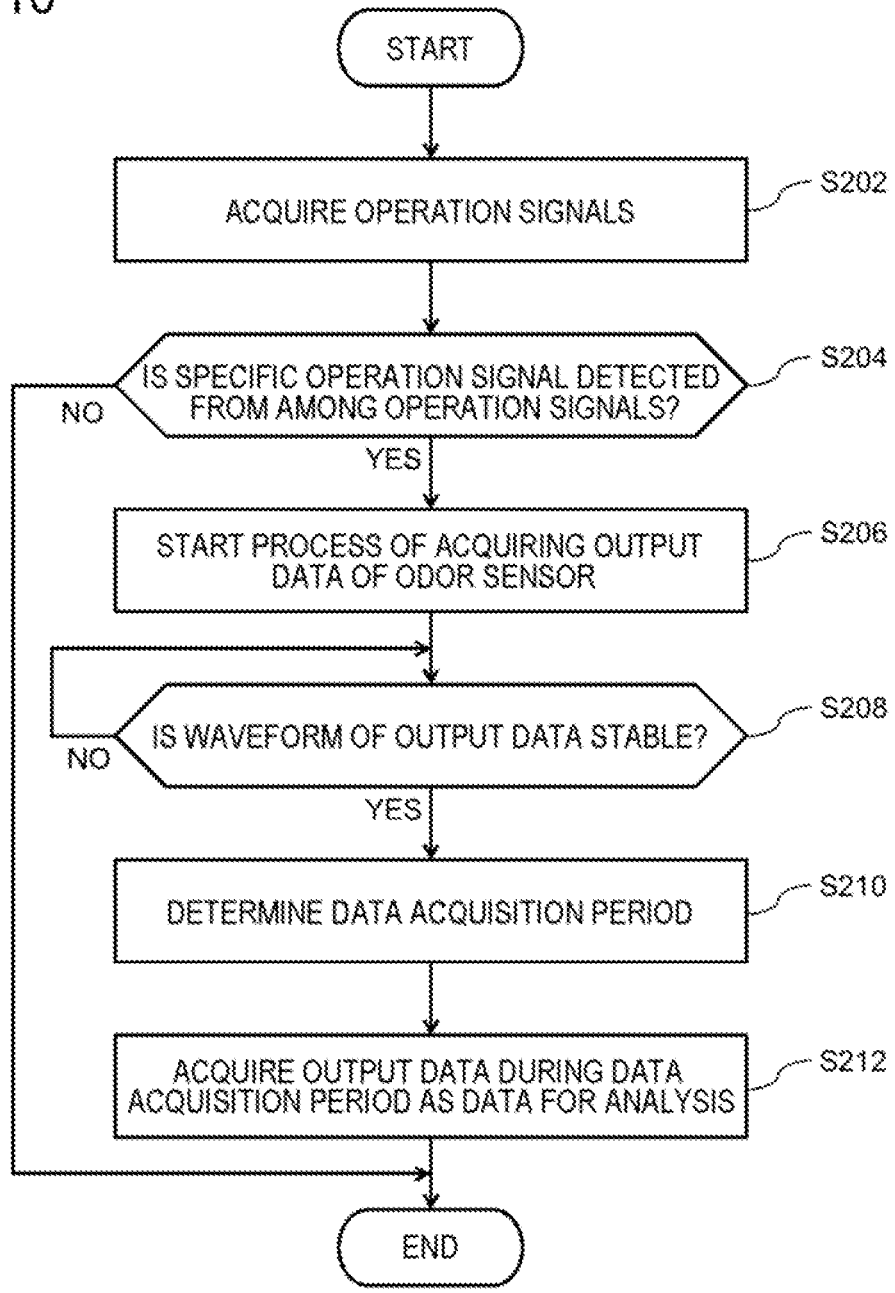
FIG. 10 is a flowchart illustrating a flow of a process which is executed by the control apparatus of the second example embodiment.

FIG. 10 is a flowchart illustrating a flow of a process which is executed by the control apparatus 10 of the second example embodiment.

The signal detection unit 110 acquires operation signals of the processing apparatus 20 (S202). Then, the signal detection unit 110 determines whether or not a specific operation signal is detected from among the operation signals acquired in the process of S202 (S204). The processes of S202 and S204 are similar to the processes of S102 and S104 of FIG. 4.

When the specific operation signal is detected from among the operation signals acquired in the process of S202 (S204: Yes), the data acquisition unit 122 starts the process of acquiring output data of the odor sensor 30 (S206). Here, the data acquisition unit 122 may be configured to operate the odor sensor 30 in response to the detection of the specific operation signal. In this manner, by operating the odor sensor 30 only when necessary, an advantageous effect of suppressing degradation of the performance of the odor sensor 30 can be expected.

With respect to the output data of the odor sensor 30 acquired by the process of S206, the data extraction unit 124 determines whether the waveform of the output data is stable or not (S208). When the waveform of the output data of the odor sensor 30 is not stable (S208: NO), the data extraction unit 124 stands by until determining that the waveform of the output data of the odor sensor 30 is stable. For example, when the variation of the amplitude of the waveform of the output data of the odor sensor 30 has decreased to a predetermined threshold or less, the data extraction unit 124 can determine that the waveform of the output data of the odor sensor 30 is stable. Responding to the determination that the waveform of the output data of the odor sensor 30 is stable (S208: YES), the data extraction unit 124 determines a period (data acquisition period) for acquiring data for analysis (S210). Specifically, the data extraction unit 124 sets, as a start point of the data acquisition period, a time point when the waveform of the output data of the odor sensor 30 is determined to be stable. Further, the data extraction unit 124 sets, as an end point of the data acquisition period, a time point after a predetermined time from the start point. Then, the data extraction unit 124 acquires, as data for analysis, output data which are output from the odor sensor 30 during the data acquisition period determined in the process of S210 (S212). The data extraction unit 124 stores the data for analysis acquired in S212 in a predetermined storage unit such as the storage device 1040.

As described above, in the present example embodiment, like the first example embodiment, the data acquisition period (the period in which the odor is stable) is determined based on the waveform of the output data of the odor sensor 30, and the output data that are output from the odor sensor 30 during this period is acquired as the data for analysis. Thereby, advantageous effects similar to those in the first example embodiment can be acquired. Note that in the present example embodiment, since the acquisition period of the data for analysis is determined based on the waveform of the output data of the odor sensor 30, an advantageous effect that the data for analysis are acquired with higher precision than in the first example embodiment can be expected.

Third Embodiment

The processing apparatus 20 requires periodical maintenance work (cleaning, replenishment of material, and the like), and there is a case in which the maintenance work is performed during the data acquisition period. In this case, due to the opening and closing of a door for maintenance of the processing apparatus 20, there is a possibility that the atmosphere of the range of measurement of the odor sensor 30 changes and stable output data cannot be acquired from the odor sensor 30. A control apparatus 10 of the present example embodiment further includes a function for solving this problem.

<Functional Configuration Example of Control Apparatus 10>

Figure 11:
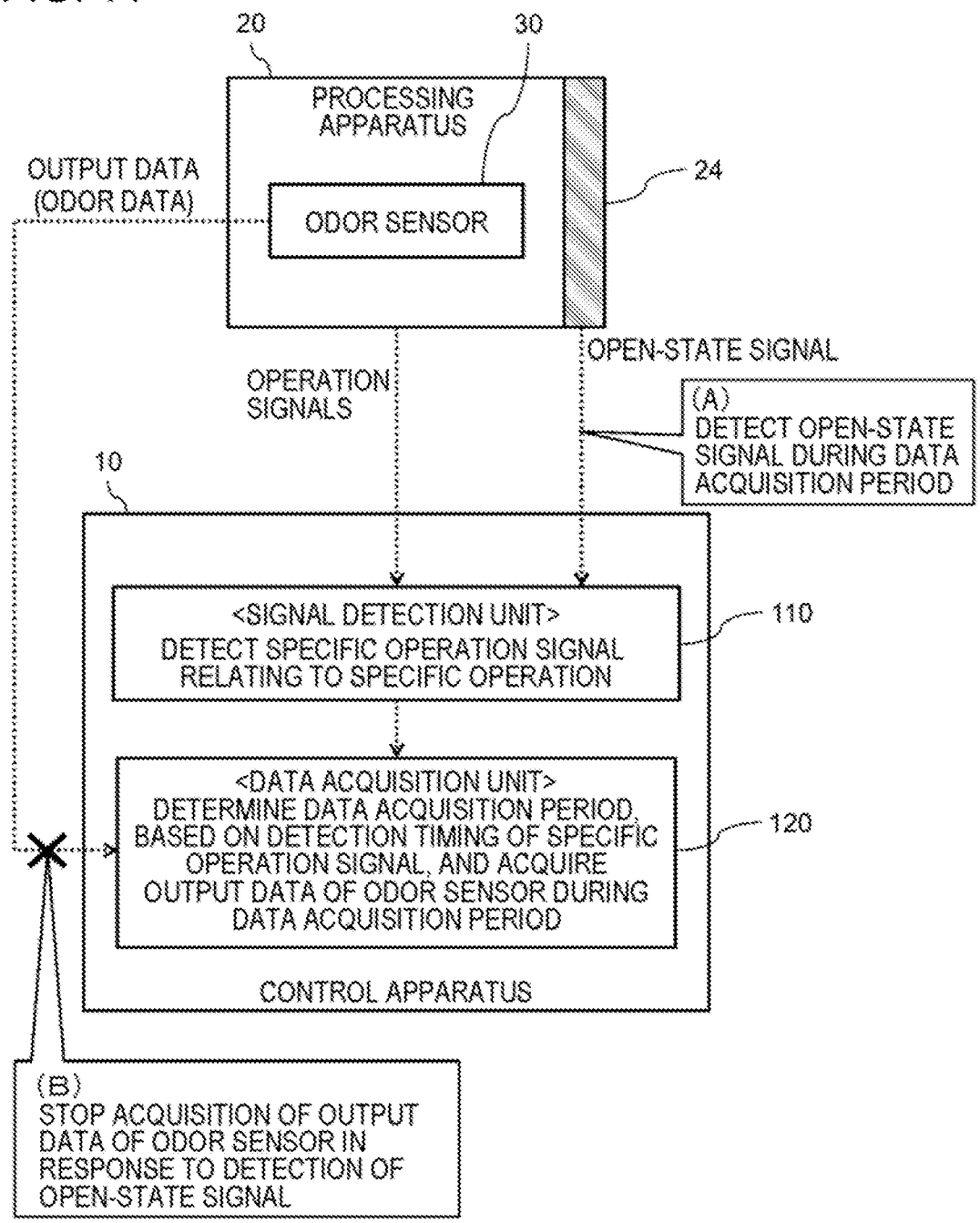
FIG. 11 is a diagram illustrating an outline of an operation of a control apparatus according to a third example embodiment.

FIG. 11 is a diagram illustrating an outline of an operation of the control apparatus 10 according to the third example embodiment. Note that the control apparatus 10 illustrated in FIG. 11 is based on the configuration of the first example embodiment. Although not illustrated, the control apparatus 10 of the present example embodiment may be based on the configuration described in the second example embodiment.

The signal detection unit 110 of the present example embodiment further detects a signal (hereinafter referred to as "open-state signal") indicating that a door 24 of the processing apparatus 20 is in an open state (A in the Figure). Here, the door 24 is a door which is opened and closed at a time of maintenance work of the processing apparatus 20. When the open-state signal is detected by the signal detection unit 110 during the data acquisition period, the data acquisition unit 120 of the present example embodiment suspends the acquisition of the output data of the odor sensor 30 (B in the Figure). Specifically, the data acquisition unit 120 acquires, as data for analysis, the output data which are output from the odor sensor 30 until the detection time point of the open-state signal from the start point of the data acquisition period.

<Flow of Process>

Figure 12:
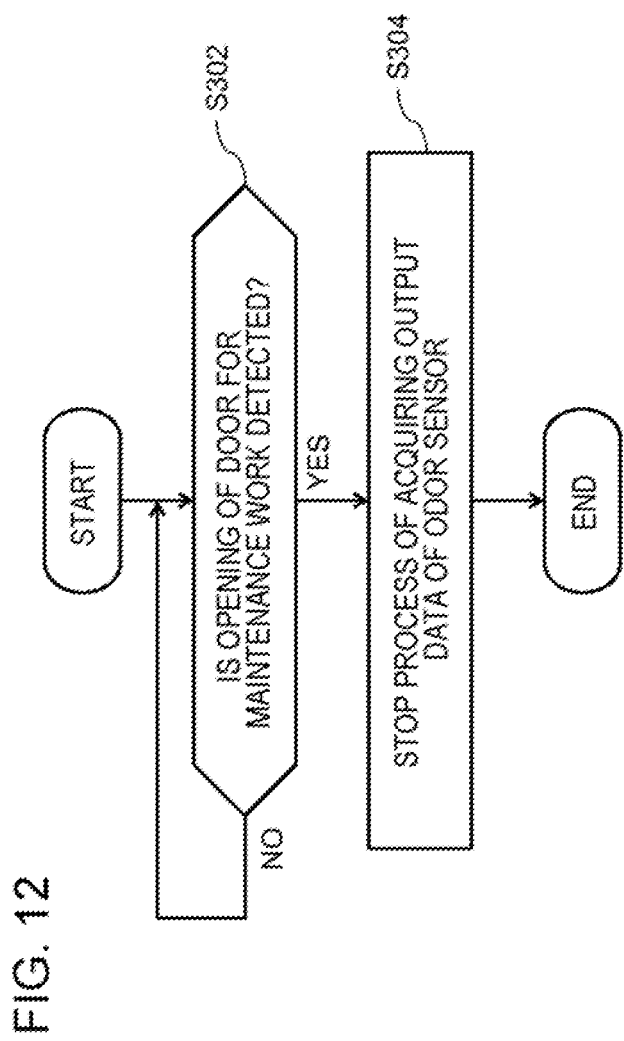
FIG. 12 is a flowchart illustrating a flow of a process which is executed by the control apparatus of the third example embodiment.

FIG. 12 is a flowchart illustrating a flow of a process which is executed by the control apparatus 10 of the third example embodiment. The process illustrated in FIG. 12 is executed during the data acquisition period determined in the process of S106 of FIG. 4.

To start with, the signal detection unit 110 monitors whether or not the door 24 for maintenance work is opened during the data acquisition period (S302). For example, the signal detection unit 110 can determine the open or closed state of the door 24 by monitoring an output signal of an opening/closing sensor (not illustrated) provided on the processing apparatus 20 in order to detect the open or closed state of the door 24. The opening/closing sensor outputs a signal (open-state signal) indicating that the door 24 is in an open state, when the door 24 is opened, and outputs a signal (closed-state signal) indicating that the door 24 is in a closed state, when the door 24 is closed. The signal detection unit 110 can detect that the door 24 is opened, when detecting the open-state signal as the output of the opening/closing sensor.

When the signal detection unit 110 detects the opening (open-state signal) of the door 24 (S302: YES), the data acquisition unit 120 suspends the process of acquiring the output data from the odor sensor 30 (S304). On the other hand, when the signal detection unit 110 does not detect the opening (open-state signal) of the door 24 (S302: NO), the signal detection unit 110 continues monitoring whether the door 24 for maintenance work is opened or not. As long as the opening (open-state signal) of the door 24 is not detected by the signal detection unit 110, the data acquisition unit 120 continues the process of acquiring the output data from the odor sensor 30, until the end of the data acquisition period.

As described above, in the present example embodiment, if the opening of the door 24 for maintenance work is detected during the data acquisition period, the process of outputting the output data of the odor sensor 30 is suspended even during the data acquisition period. Thereby, high-precision data for analysis can be acquired in such a manner that the output data of the odor sensor 30 after the change of the atmosphere of the range of measurement of the odor sensor 30 (i.e., the output data of an unstable waveform) are not included in the final data for analysis.

<Modification>

In the present example embodiment, the output data, which are output from the odor sensor 30 after the open-state signal is detected by the signal detection unit 110, is not used as data for analysis. Thus, the data acquisition unit 120 may be configured to stop the odor sensor 30 when the open-state signal is detected by the signal detection unit 110. By doing so, an advantageous effect of suppressing the degradation of the performance of the odor sensor 30 can be expected.

In addition, in the present example embodiment, when the period until detecting the open-state signal from the start point of the data acquisition period (i.e., the period in which the output data of the odor sensor 30 are actually acquired) is too short, there is a possibility that sufficient data for analysis are not acquired. Thus, when the length of the period until detecting the open-state signal from the start point of the data acquisition period is less than a predetermined threshold, the data acquisition unit 120 may be configured to discard the output data acquired during the period. Thereby, it is possible to prevent the storage area of the control apparatus 10 from being occupied by unnecessary data.

Fourth Embodiment

There is a case where, after a data acquisition period (a first data acquisition period) is determined based on a detection timing of a specific operation signal (a first specific operation signal), a new specific operation signal (a second specific operation signal) is detected before the data acquisition period or during the data acquisition period. In this case, due to the overlapping between the first data acquisition period and the timing of processing food and drink by the processing apparatus 20, there is a possibility that the atmosphere of the range of measurement of the odor sensor 30 changes and stable output data cannot be acquired from the odor sensor 30. A control apparatus 10 of the present example embodiment further includes a function for solving this problem.

<Functional Configuration Example of Control Apparatus 10>

Figure 13:
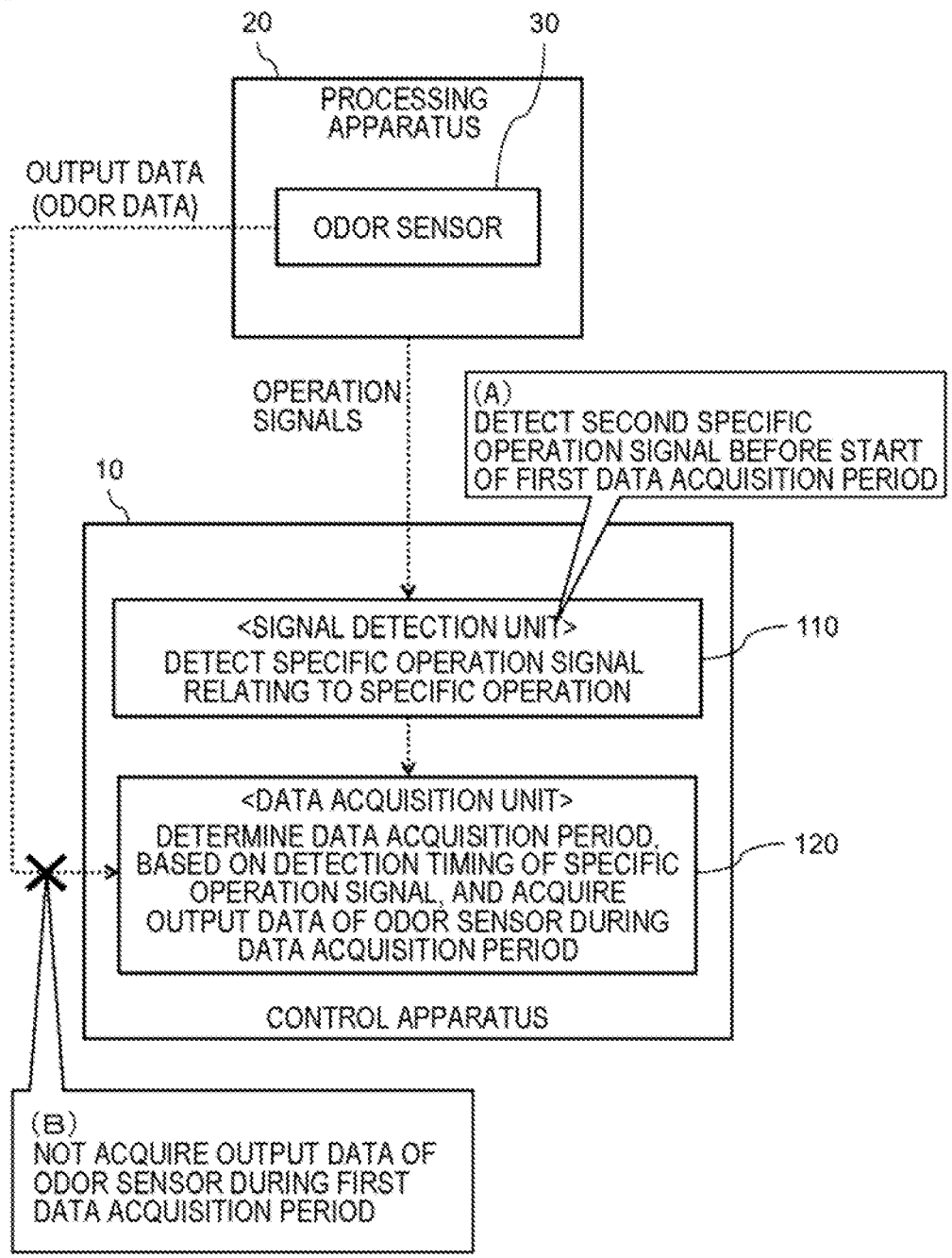
FIG. 13 is a diagram illustrating an outline of an operation of a control apparatus according to a fourth example embodiment.
Figure 14:
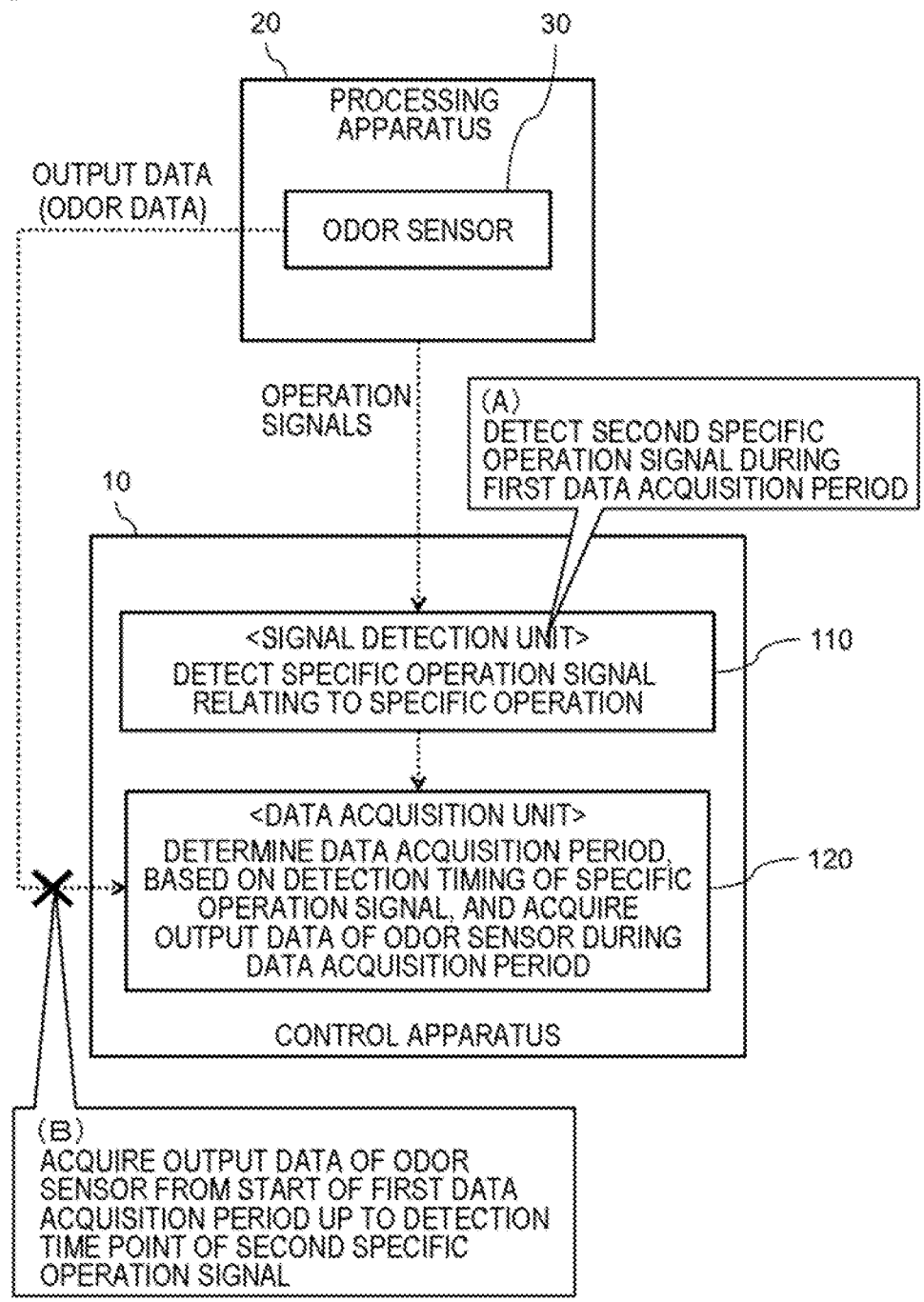
FIG. 14 is a diagram illustrating an outline of an operation of the control apparatus according to the fourth example embodiment.

FIG. 13 and FIG. 14 are diagrams illustrating outlines of operations of the control apparatus 10 according to the fourth example embodiment. Note that the control apparatus 10 illustrated in FIG. 13 and FIG. 14 is based on the configuration of the first example embodiment. Although not illustrated, the control apparatus 10 of the present example embodiment may be based on the configuration described in the second example embodiment.

As illustrated in FIG. 13, when a second specific operation signal is detected before a first data acquisition period associated with a first specific operation signal (A in the Figure), the data acquisition unit 120 of the present example embodiment is configured to not acquire output data of the odor sensor 30 in the first data acquisition period (B in the Figure). Note that, in this case, if still another specific operation signal is not detected until the start of a second acquisition period associated with the second specific operation signal, the data acquisition unit 120 acquires, as data for analysis, output data of the odor sensor 30 in the second data acquisition period.

In addition, as illustrated in FIG. 14, when a second specific operation signal is detected during a first data acquisition period associated with a first specific operation signal (A in the Figure), the data acquisition unit 120 of the present example embodiment acquires, as data for analysis, output data of the odor sensor 30 up to a detection time point of the second specific operation signal from the start point of the first data acquisition period (B in the Figure). <Flow of Process>

FIG. 15 is a flowchart illustrating an example of a flow of a process which is executed by the control apparatus 10 of the fourth example embodiment.

The signal detection unit 110 acquires operation signals of the processing apparatus 20 (S402). Then, the signal detection unit 110 determines whether or not a specific operation signal (first specific operation signal) is detected from among the operation signals acquired in the process of S402 (S404). When the specific operation signal is detected from among the operation signals (S404: YES), the data acquisition unit 120 determines a period (data acquisition period) for acquiring odor data which are output from the odor sensor 30 (S406). These processes are similar to the processes of S102 to S106 of FIG. 4.

Here, when a new specific operation signal (second specific operation signal) is detected by the signal detection unit 110 before the start of the data acquisition period determined by the process of S406 (S408: YES), the data acquisition unit 120 re-determines the data acquisition period, based on the detection timing of the second specific operation signal (S406). When this process is executed, the data acquisition unit 120 does not acquire, as data for analysis, the output data which are output from the odor sensor 30 during the data acquisition period (first data acquisition period) associated with the first specific operation signal.

On the other hand, when the first data acquisition period starts without the detection of the second specific operation signal (S408: NO), the data acquisition unit 120 acquires, as data for analysis, the output data which are output from the odor sensor 30 during the first data acquisition period (S410).

Here, when the second specific operation signal is detected by the signal detection unit 110 during the first data acquisition period (S412: YES), the data acquisition unit 120 suspends the process of acquiring the output data from the odor sensor 30 even during the first data acquisition period (S414). Specifically, the data acquisition unit 120 acquires the output data which are output from the odor sensor 30 from the start point of the first data acquisition period up to the detection time point of the second specific operation signal. On the other hand, when the first data acquisition period ends without the detection of the second specific operation signal (S412: NO), the data acquisition unit 120 acquires the output data which are output from the odor sensor 30 from the start point to the end point of the first data acquisition period. In addition, the data acquisition unit 120 stores the output data of the odor sensor 30, which are acquired by the above-described process, as the data for analysis in a predetermined storage unit such as the storage device 1040.

As described above, in the present example embodiment, when a new specific operation signal (the new execution of an operation involving the occurrence of an odor by the processing apparatus 20) is detected before the data acquisition period, the process of acquiring output data of the odor sensor 30 is not executed during the data acquisition period. In addition, when a new specific operation signal (the new execution of an operation involving the occurrence of an odor by the processing apparatus 20) is detected during the data acquisition period, the process of acquiring output data of the odor sensor 30 is suspended even during the data acquisition period. In this manner, high-precision data for analysis can be acquired by not acquiring the output data of the odor sensor 30 in the period in which there is a possibility that the atmosphere of the range of measurement of the odor sensor 30 changes (i.e., the period in which there is a possibility that output data of an unstable waveform are included).

The example embodiments of the present invention have been described above with reference to the drawings. The present invention should not be construed by being limited to these example embodiments. Various changes, improvements or the like can be made based on the knowledge of a person skilled in the art, without departing from the spirit of the present invention. Various inventions can be made by properly combining structural elements disclosed in the example embodiments. For example, some structural elements may be omitted from all the structural elements disclosed in the example embodiments, or structural elements of different example embodiments may be combined.

In addition, in the flowcharts used in the above description, steps (processes) are described in order. The order of execution of steps executed in each example embodiment is not limited to the described order. In each example embodiment, the order of the illustrated steps may be changed within the scope in which no problem occurs in the contents of the steps. Moreover, the above-described example embodiments may be combined within the scope in which the contents thereof are not inconsistent.

What is claimed is:

1. A control apparatus comprising:
a memory storing instructions; and
one or more processors configured to execute the instructions to:
acquire operation signals relating to an operation of a processing apparatus that processes food and drink;
detect a specific operation signal relating to a specific operation from among the operation signals;
determine, based on a detection timing of the specific operation signal, a data acquisition period of an odor sensor provided in the processing apparatus; and
acquire output data being output from the odor sensor during the data acquisition period, wherein
determination of the data acquisition period comprises setting, as a start point of the data acquisition period, a time point after passage of a reference time from a detection time point of the specific operation signal.

2. The control apparatus according to claim 1, wherein the one or more processors are further configured to execute the instructions to operate the odor sensor in response to detection of the specific operation signal.

3. The control apparatus according to claim 1, wherein the reference time is determined based on a kind of the food and drink provided from the processing apparatus.

4. The control apparatus according to claim 1, wherein, the one or more processors are further configured to execute the instructions not to acquire, when a second specific operation signal is detected before a first data acquisition period associated with a first specific operation signal, output data of the odor sensor during the first data acquisition period.

5. The control apparatus according to claim 1, wherein, the one or more processors are further configured to execute the instructions to acquire, when a second specific operation signal is detected during a first data acquisition period associated with a first specific operation signal, output data of the odor sensor from a start point of the first data acquisition period up to a detection time point of the second specific operation signal.

6. The control apparatus according to claim 1, wherein the one or more processors are further configured to execute the instructions to detect, as the specific operation signal, a signal to be sent in response to depression of a purchase button of the food and drink, the purchase button being provided on the processing apparatus.

7. The control apparatus according to claim 1, wherein the one or more processors are further configured to execute the instructions to:
acquire a current signal being output from a current sensor provided in the processing apparatus; and
detect the specific operation signal, based on a waveform of the current signal.

8. The control apparatus according to claim 1, wherein the one or more processors are further configured to execute the instructions to:
acquire an acoustic signal being output from an acoustic sensor provided in the processing apparatus; and
detect the specific operation signal, based on a waveform of the acoustic signal.

9. The control apparatus according to claim 1, wherein the processing apparatus includes a door that opens and closes at a time of maintenance, and
the one or more processors are further configured to execute the instructions to acquire, when an open-state signal indicating that the door is in an open state is detected by the signal detection unit during the data acquisition period, output data of the odor sensor from the start point of the data acquisition period up to a detection time point of the open-state signal.

10. The control apparatus according to claim 9, wherein the one or more processors are further configured to execute the instructions to stop the odor sensor when the open-state signal is detected.

11. The control apparatus according to claim 1, wherein the processing apparatus is an apparatus that cooks a drink.

12. The control apparatus according to claim 1, wherein the reference time is determined based on a time required until a waveform of the output data became a stable waveform.

13. A data acquisition method performed by a computer and comprising:
acquiring operation signals relating to an operation of a processing apparatus that processes food and drink;
detecting a specific operation signal relating to a specific operation from among the operation signals;
determining, based on a detection timing of the specific operation signal, a data acquisition period of an odor sensor provided in the processing apparatus; and
acquiring output data being output from the odor sensor during the data acquisition period, wherein
determining the data acquisition period comprises setting, as a start point of the data acquisition period, a time point after passage of a reference time from a detection time point of the specific operation signal.

* * * * *